(12) United States Patent
Wildeman

(10) Patent No.: US 6,855,220 B2
(45) Date of Patent: Feb. 15, 2005

(54) FASTENER FABRIC AND RELATED METHOD

(75) Inventor: Martin Wildeman, Spartanburg, SC (US)

(73) Assignee: Tietex International, Ltd., Spartanburg, SC (US)

( * ) Notice: Subject to any disclaimer, the term of this patent is extended or adjusted under 35 U.S.C. 154(b) by 0 days.

(21) Appl. No.: 10/315,718

(22) Filed: Dec. 10, 2002

(65) Prior Publication Data

US 2004/0022993 A1 Feb. 5, 2004

Related U.S. Application Data

(63) Continuation-in-part of application No. 10/212,333, filed on Aug. 5, 2002.

(51) Int. Cl.[7] .............................. A41F 1/00; B32B 3/10; B32B 31/12; B32B 31/16
(52) U.S. Cl. .............................. 156/66; 156/72; 156/93; 156/244.11; 156/308.2; 156/309.6
(58) Field of Search ........................ 156/66, 72, 92–93, 156/244.11, 308.2, 309.6, 309.9

(56) References Cited

U.S. PATENT DOCUMENTS

| | | | |
|---|---|---|---|
| 3,589,147 A | * | 6/1971 | Price et al. .................... 68/125 |
| 4,035,881 A | | 7/1977 | Zocher ........................ 28/111 |
| 4,042,453 A | | 8/1977 | Conway et al. ............. 162/108 |
| 4,739,635 A | | 4/1988 | Conley et al. ................ 66/190 |
| 4,770,917 A | | 9/1988 | Tochacek et al. ............. 428/95 |
| 4,931,343 A | | 6/1990 | Becker et al. ................ 428/95 |
| 5,119,643 A | | 6/1992 | Conley et al. ................ 66/190 |
| 5,401,554 A | * | 3/1995 | Armen ........................ 428/96 |
| 5,447,590 A | | 9/1995 | Gilpatrick ................... 156/178 |
| 5,462,766 A | * | 10/1995 | Markusch et al. .......... 427/244 |
| 5,654,066 A | | 8/1997 | Pacione ....................... 428/95 |
| 5,664,441 A | | 9/1997 | Clerici ........................ 66/193 |
| 5,692,949 A | | 12/1997 | Sheffield et al. ............ 451/538 |
| 5,695,845 A | | 12/1997 | Ogawa et al. ................ 428/93 |
| 5,725,927 A | | 3/1998 | Zilg et al. .................... 428/89 |
| 5,740,578 A | | 4/1998 | Moore ....................... 15/147.2 |
| 5,789,058 A | | 8/1998 | Usher et al. .................. 428/88 |
| 5,962,102 A | | 10/1999 | Sheffield et al. ............. 428/92 |
| 6,428,526 B1 | | 8/2002 | Heindel et al. ............. 604/391 |
| 2002/0132084 A1 | * | 9/2002 | Fink et al. .................... 428/85 |

* cited by examiner

*Primary Examiner*—Sam Chuan Yao
(74) *Attorney, Agent, or Firm*—J. M. Robertson Intellectual Prop. LLC

(57) ABSTRACT

A composite sheet material for use as a portion of a tear away fastening system. The sheet material includes a substrate layer and yarns extending through the substrate layer such that the define an arrangement of looped elements projecting away from one side of the substrate layer. The looped elements are interconnected by portions of the yarns disposed across the other side of the substrate layer. A backing layer is disposed in overlying relation to the substrate layer to hold the yarns in place.

15 Claims, 16 Drawing Sheets

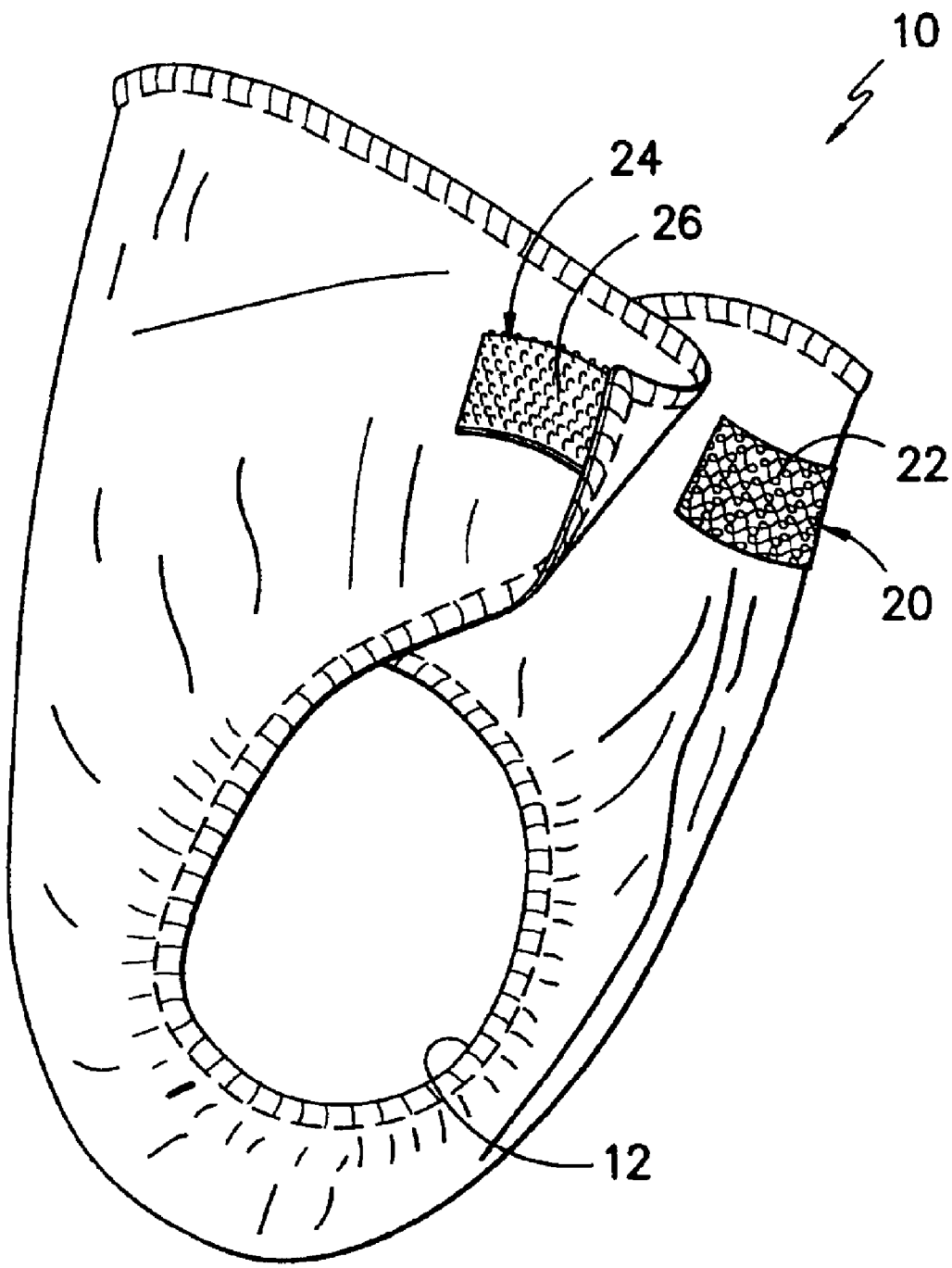
FIG. -1-

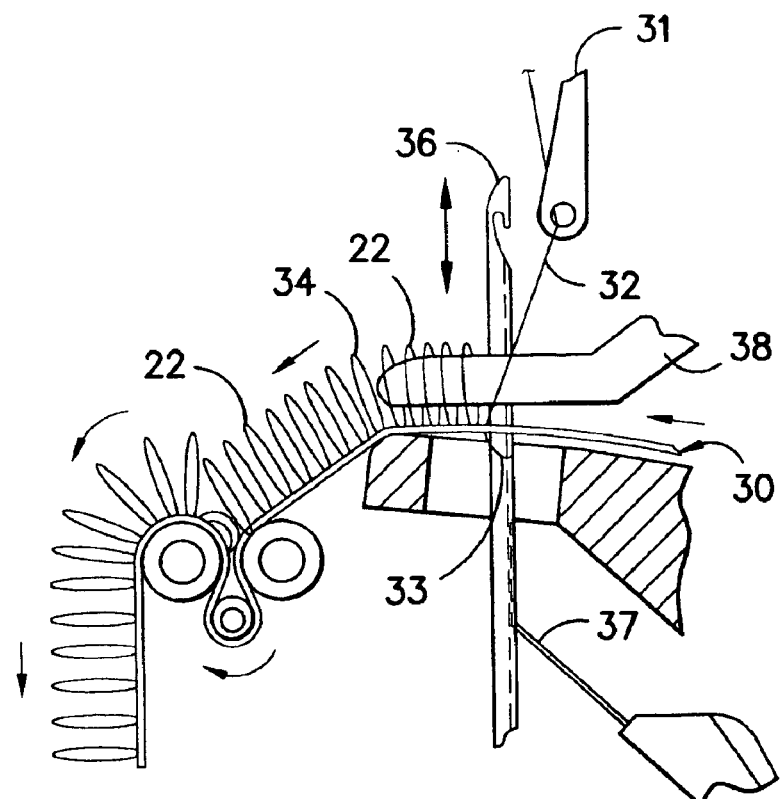
FIG. -2-
PRIOR ART
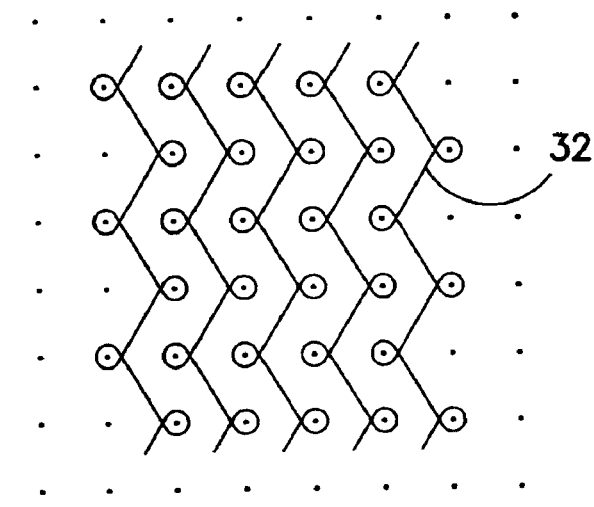
FIG. -3-
PRIOR ART

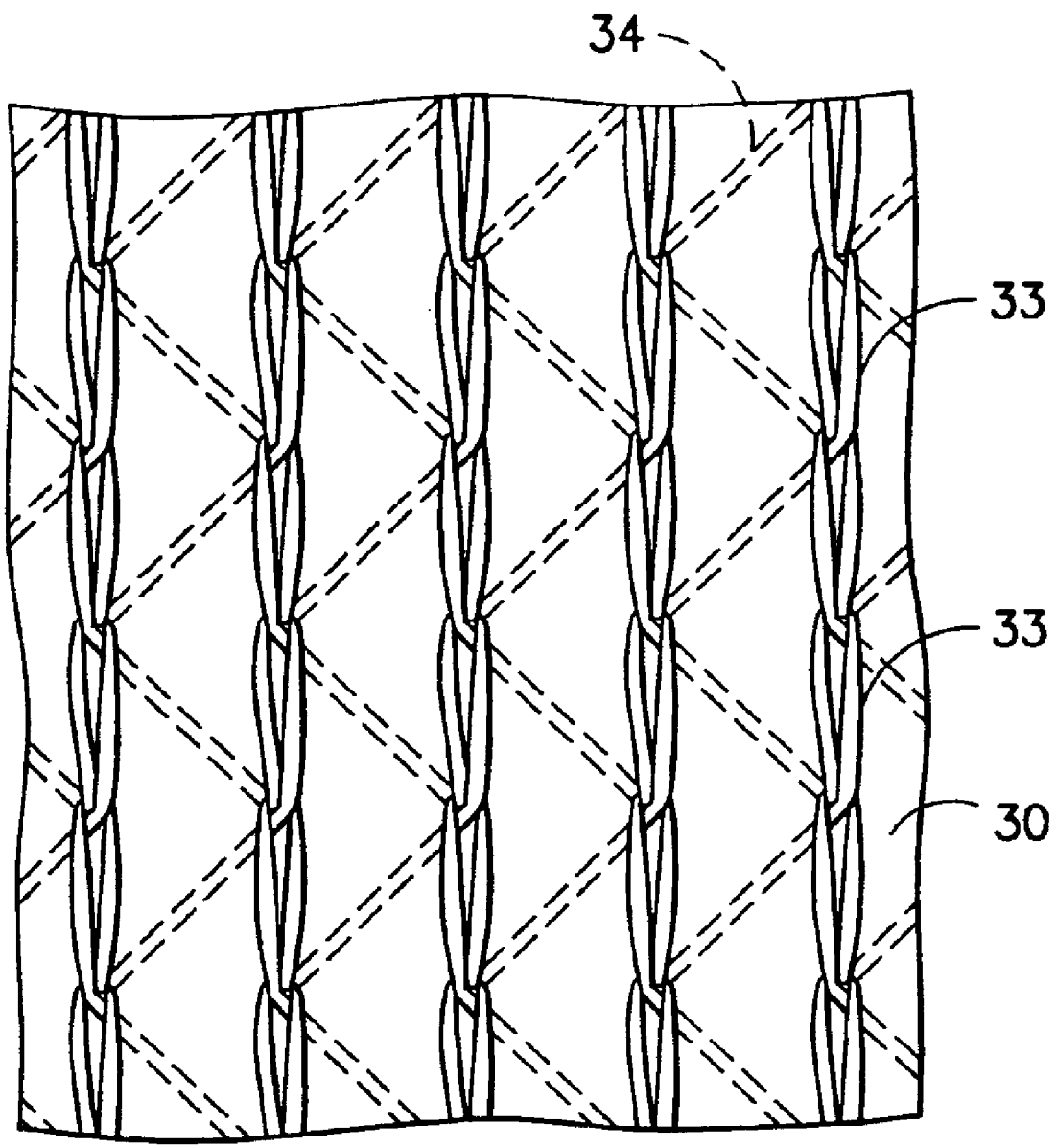
FIG. -3A-
PRIOR ART

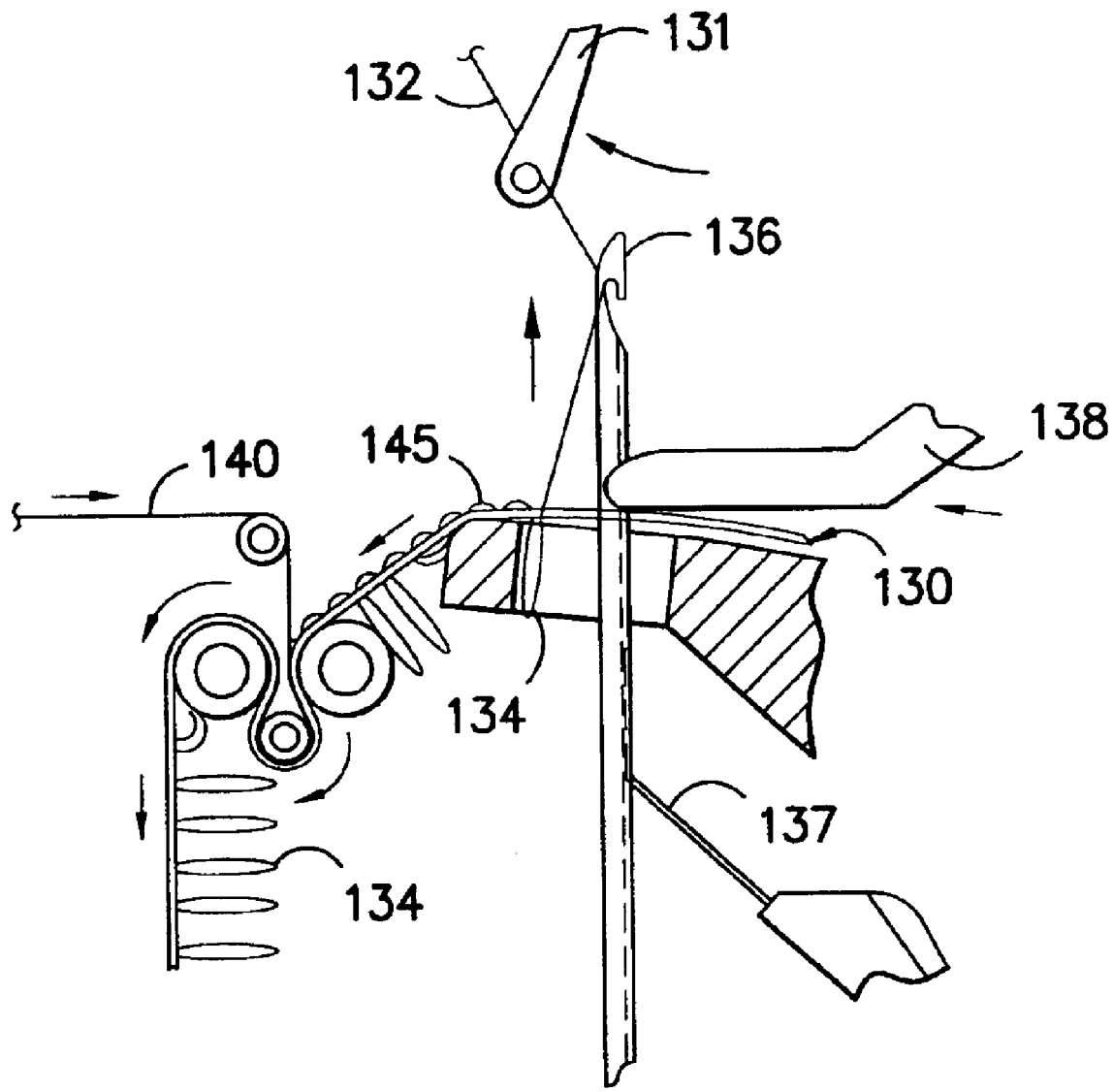
FIG. —4A—

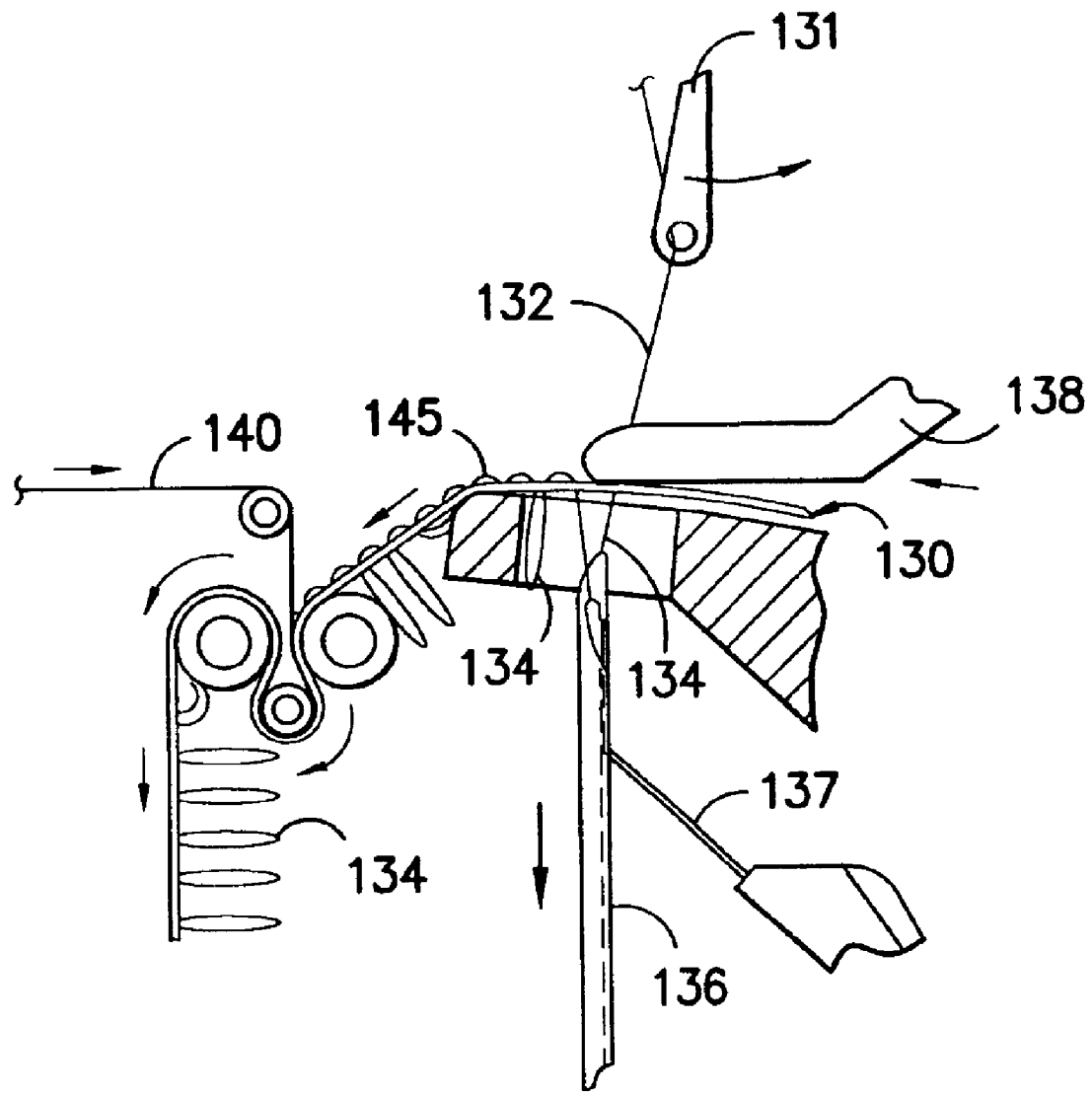
FIG. —4B—

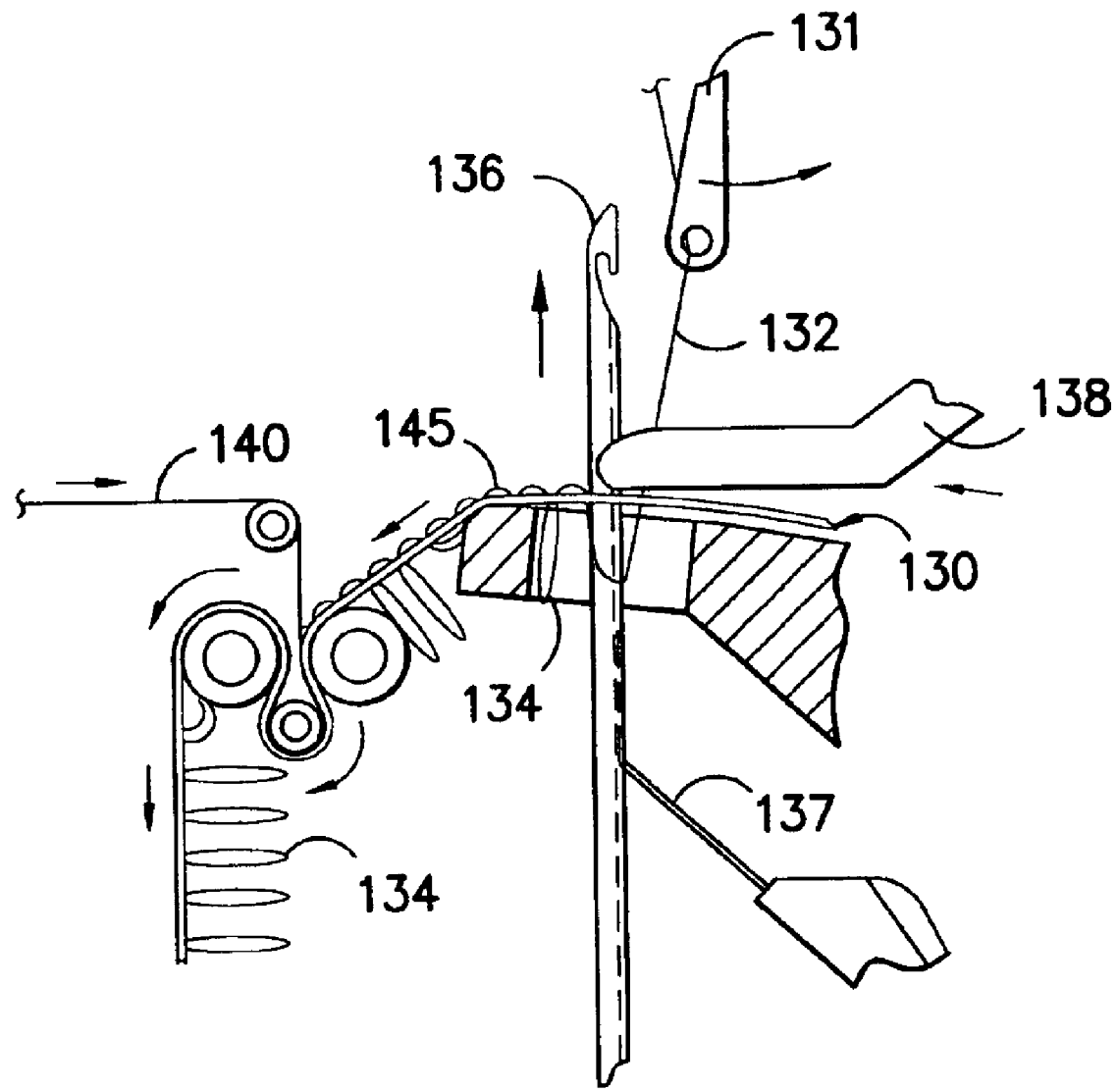
FIG. —4C—

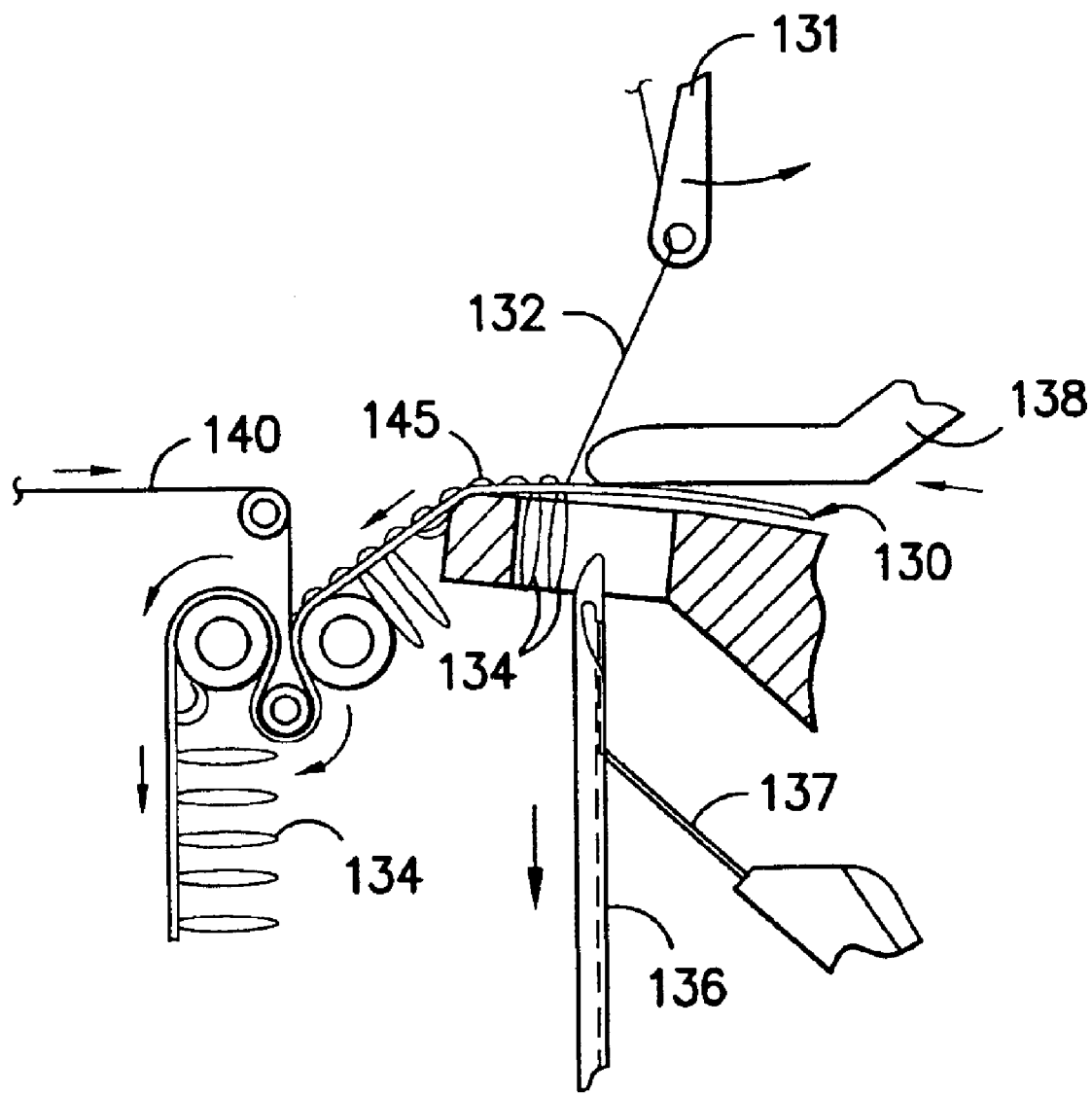
FIG. —4D—

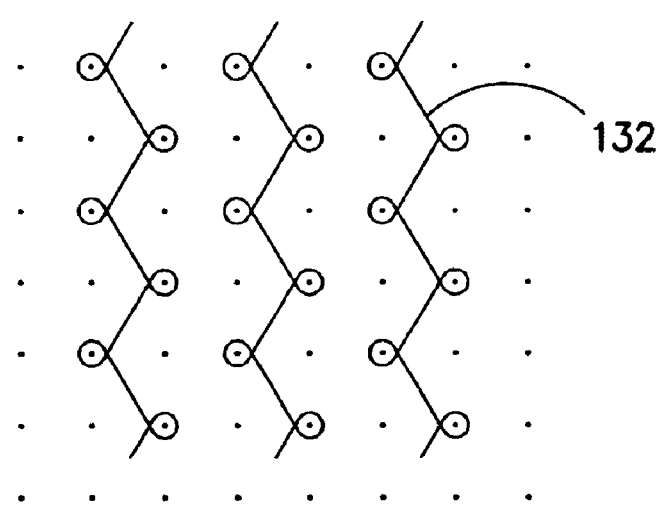
FIG. -5A-
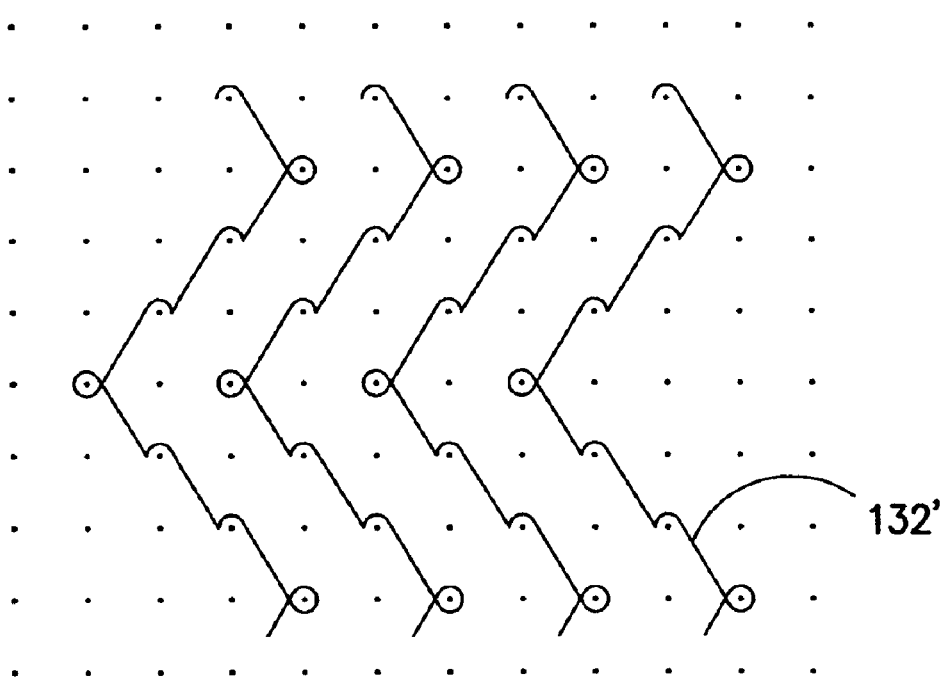
FIG. -5B-

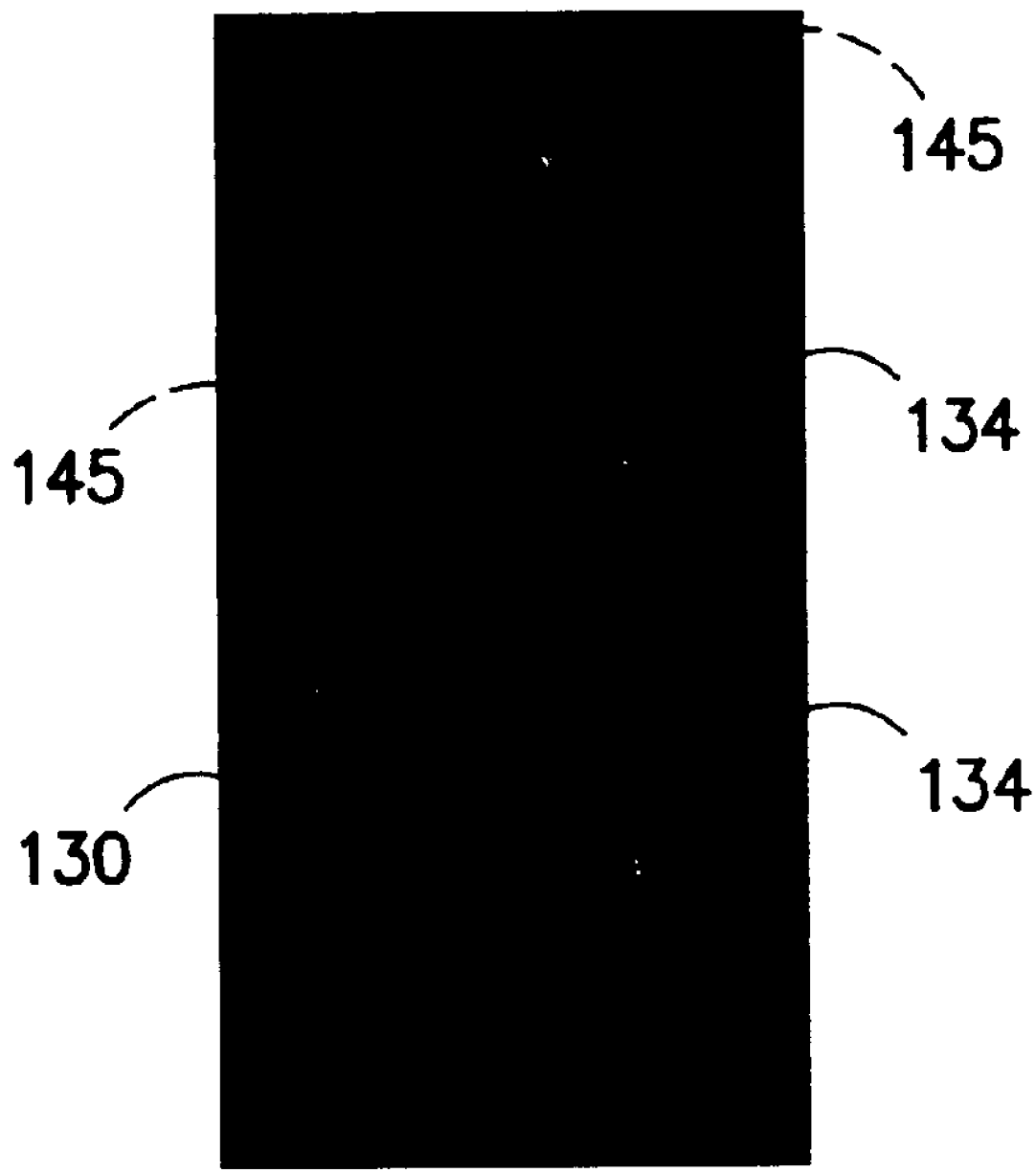
FIG. —6—

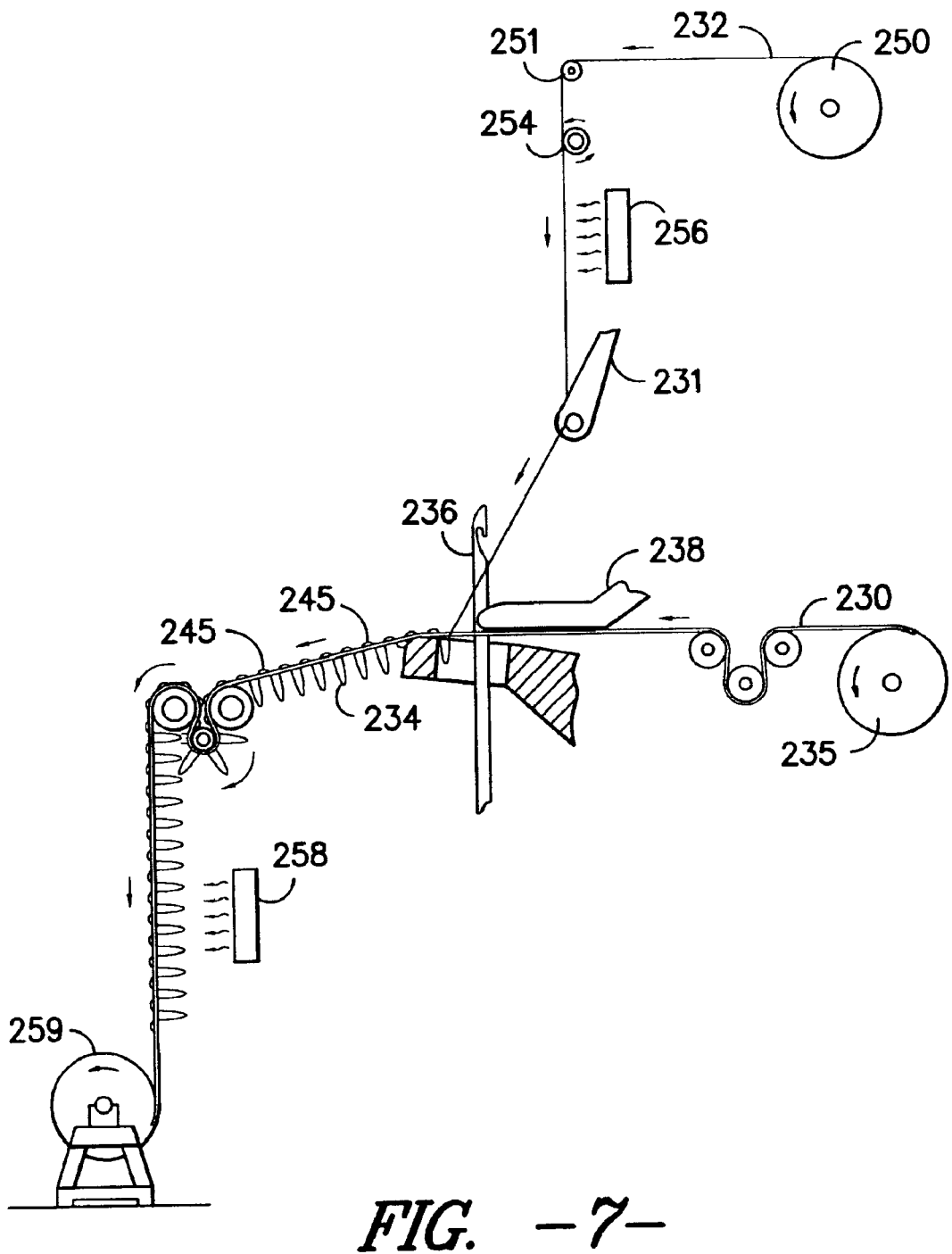
FIG. −7−

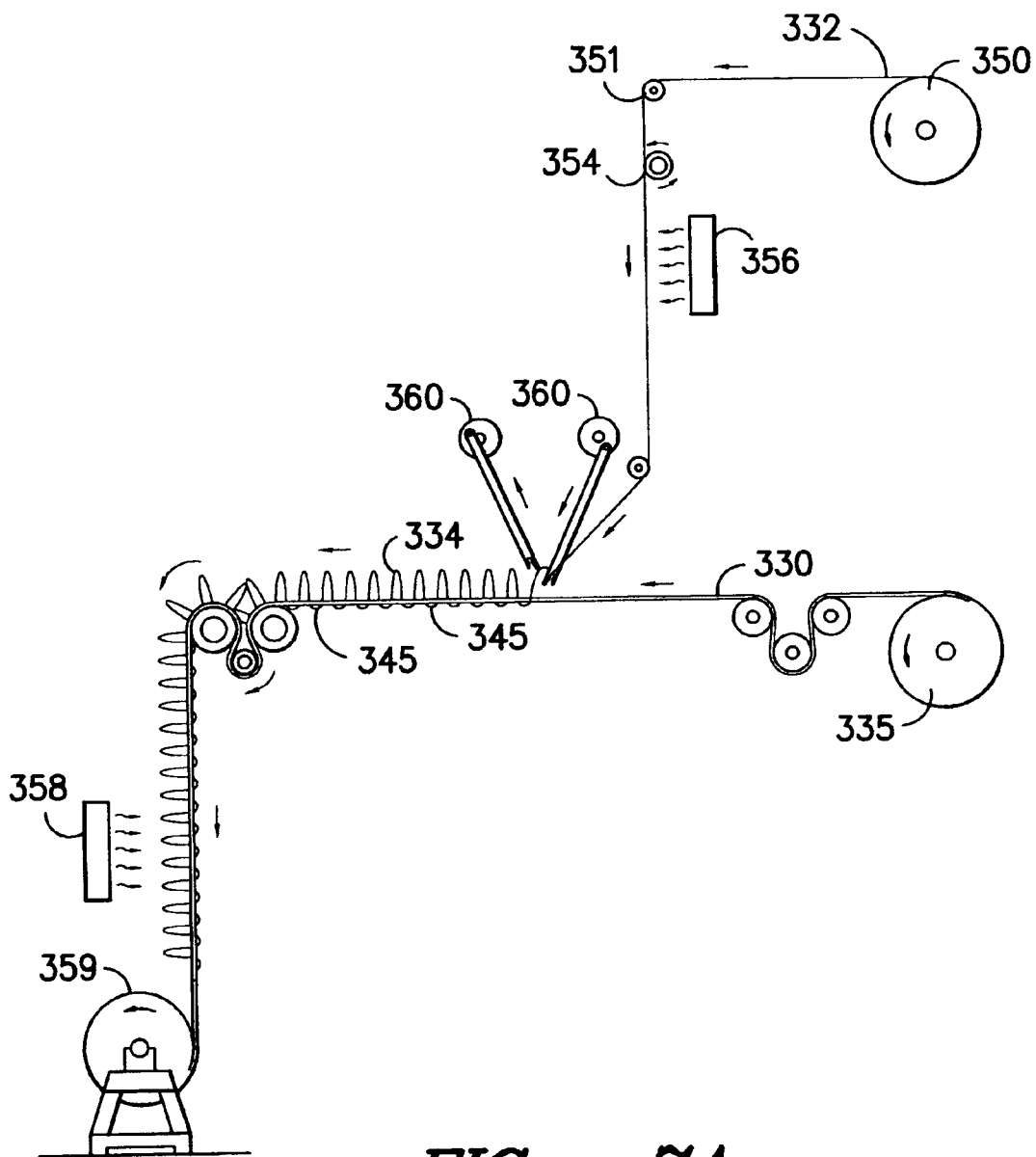
FIG. -7A-

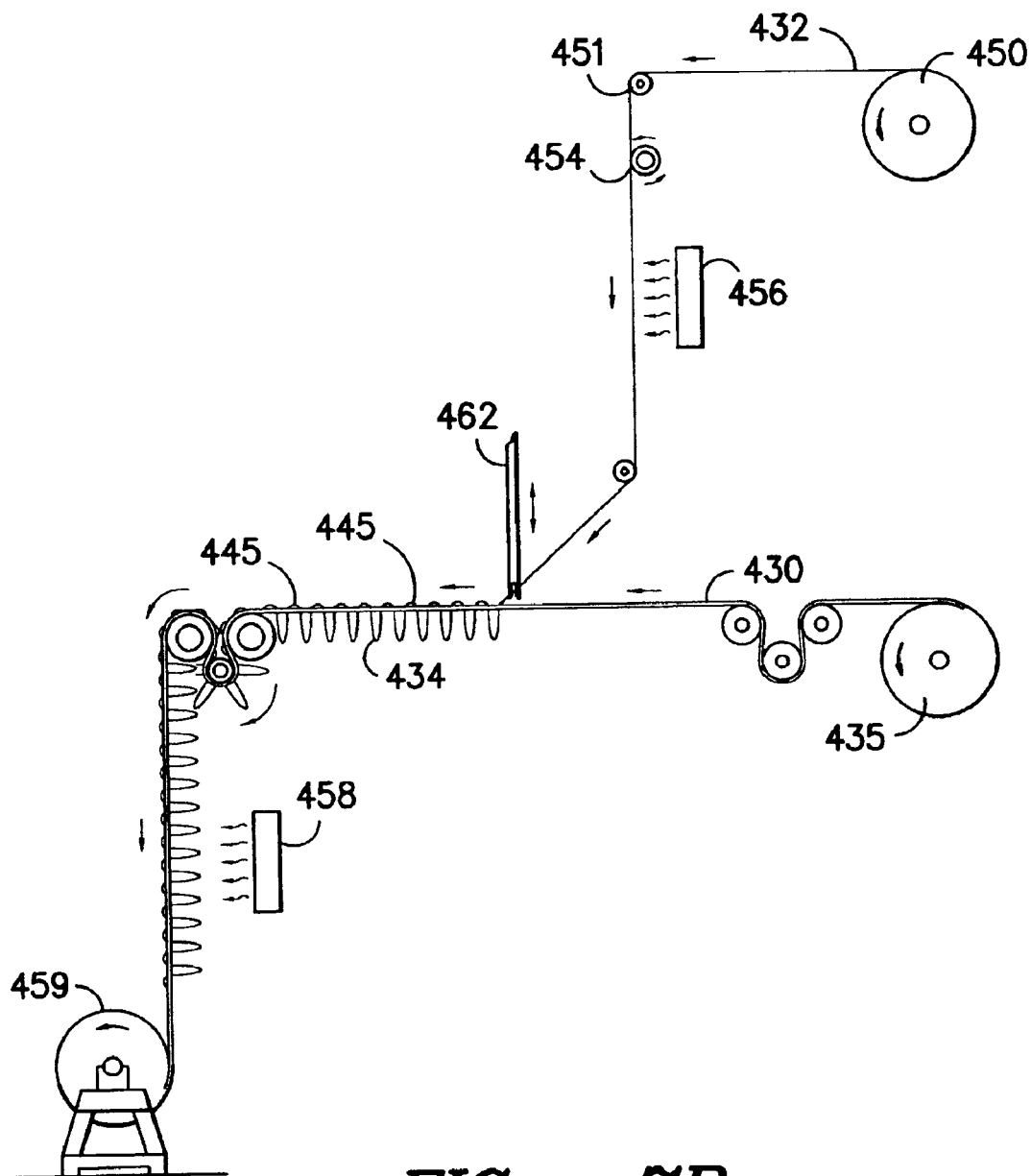
FIG. —7B—

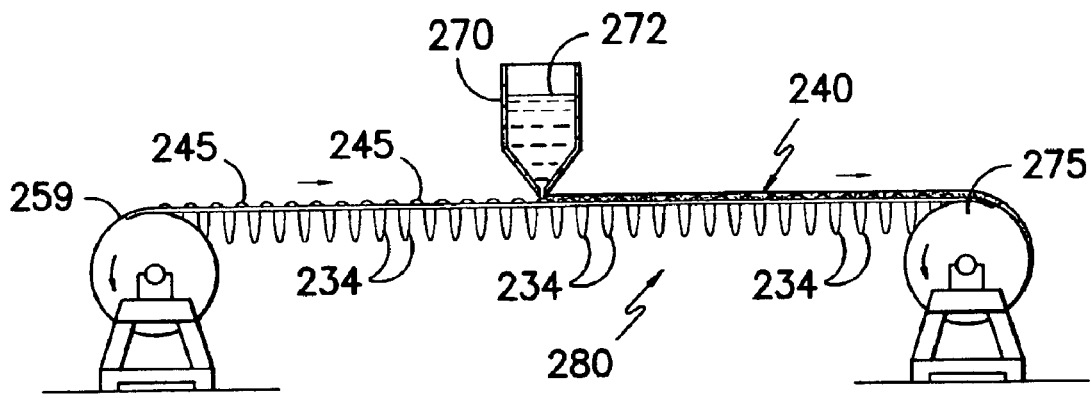
FIG. -8-
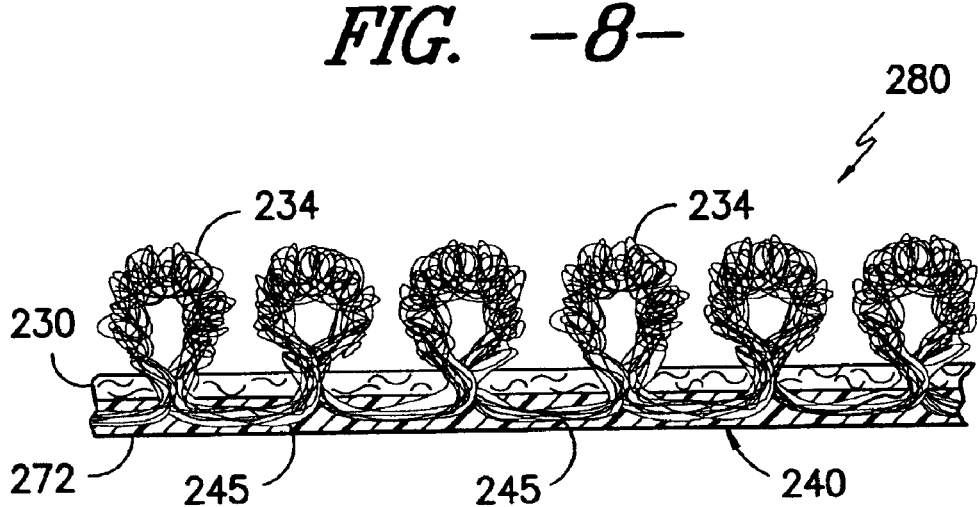
FIG. -9-
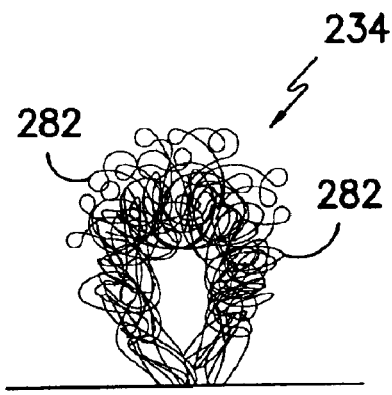
FIG. -10-

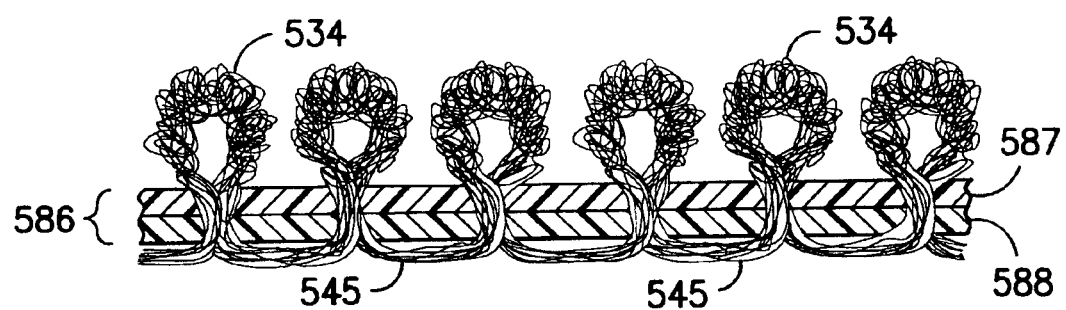
FIG. —11—
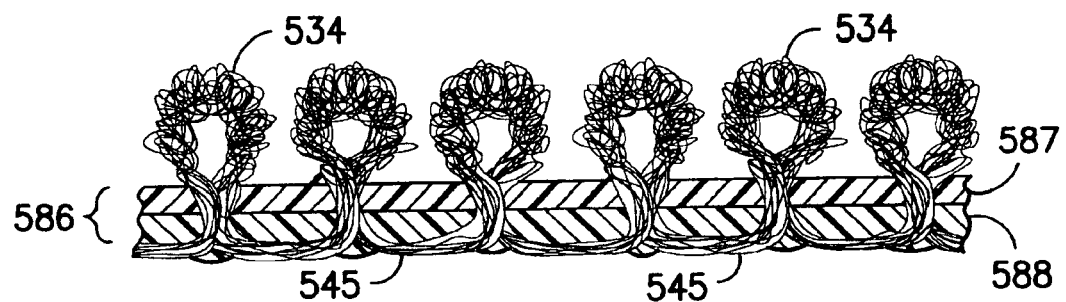
FIG. —11A—

FIG. —12A—
FIG. —12B—
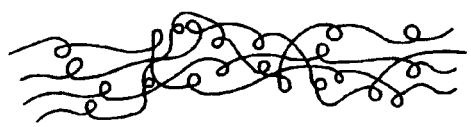
FIG. —12C—
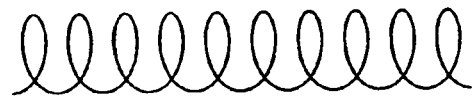
FIG. —12D—
FIG. —12E—
FIG. —12F—

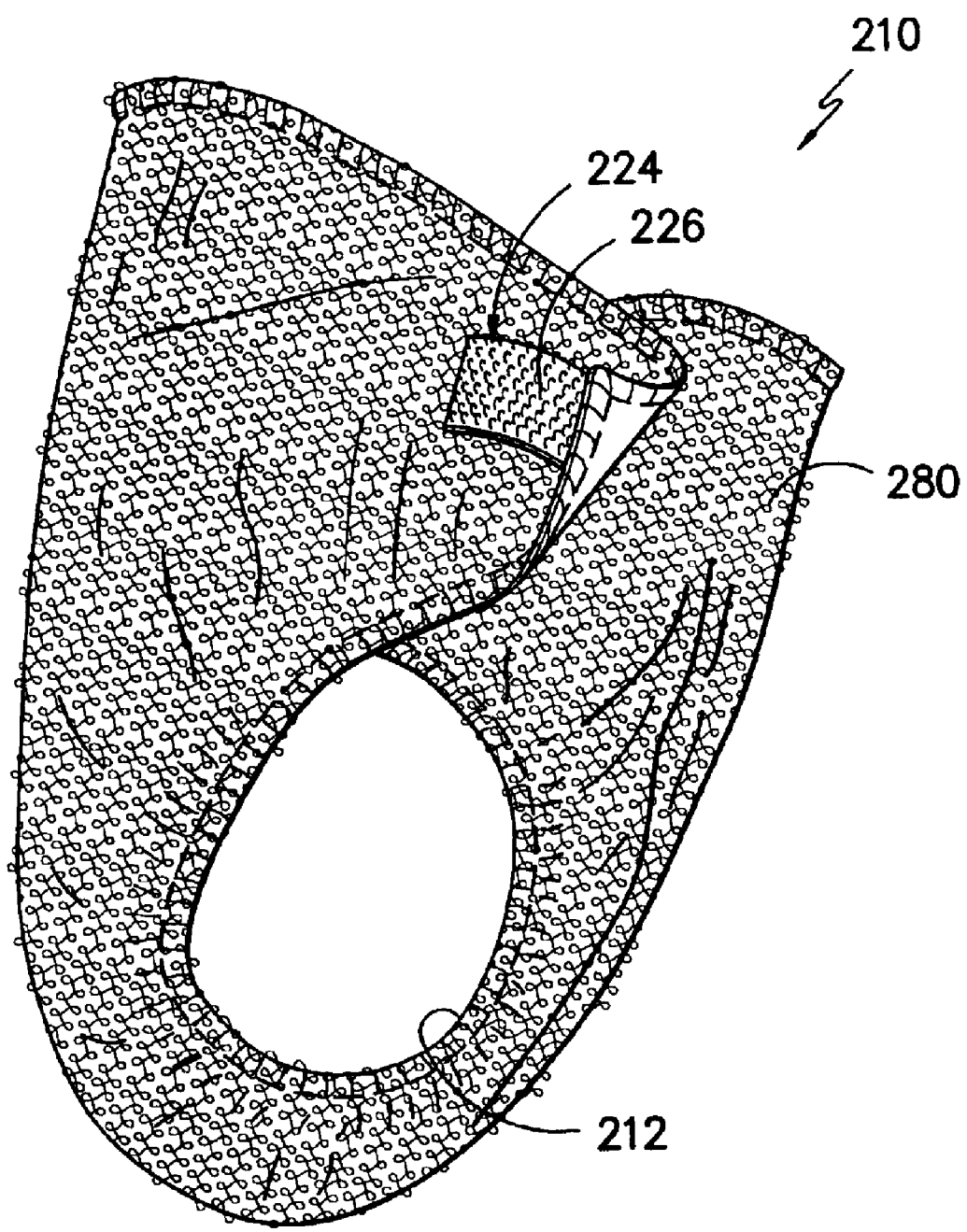
FIG. -13-

FASTENER FABRIC AND RELATED METHOD

CROSS-REFERENCE TO RELATED APPLICATION

This application is a continuation-in-part of my copending application Ser. No. 10/212,333 having a filing date of Aug. 5, 2002 the contents of which are hereby incorporated by reference as if set forth herein in their entirety.

TECHNICAL FIELD

The present invention relates to a composite material including an arrangement of spaced surface nodes disposed across at least one surface and more particularly to a composite material including an arrangement of surface nodes of filamentary construction projecting away from at least one side of a substrate layer such that the surface nodes are adapted for use as the female acceptance portion of a male/female tear away fastening system incorporating a female acceptance portion adapted to engage a cooperating hooking surface.

BACKGROUND OF THE INVENTION

Tear away or contact fastening systems are well known. Such systems incorporate two opposing segments of material which are engageable in substantially juxtaposed relation to one another. A male portion of such a contact fastening system typically incorporates a plurality of outwardly projecting hooking structures while the female portion incorporates a plurality of outwardly projecting loop structures. Upon engagement between the two cooperating portions the hooking structures engage the opposing loop structures thereby establishing a bond between the two opposing portions. This bond may be broken by the application of a peel away action between the two opposing portions of material thereby permitting the male and female portions to be progressively disengaged from one another. The engagement may be reactivated by simply bringing the male and female portions back into contacting laminar relation with one another.

In the past, the hook and loop structures defining the male and female portions of contact fastening systems have been formed by a variety of practices. According to one practice, a plurality of yarns forming the hooking and/or loop segments have been stitched through a polymeric film in a fully threaded tricot stitch to form loops projecting from a first surface of the film and to form locking portions of the stitches across a second opposite surface of the film. Such a construction is illustrated and described in U.S. Pat. No. 4,931,343 the teachings of which are incorporated by reference as is fully set forth herein. The hook portions which may be either of a classic hook configuration or which have an enlarged head which nonetheless engages the loop portion may be formed by first producing a loop portion of the material and thereafter either cutting the loops along one side to form the hooks or melting the upper portions of the loops to form projections with enlarged heads at their ends.

SUMMARY OF THE INVENTION

The present invention provides advantages and alternatives over the prior art by providing a simplified practice for forming a composite structure which incorporates an arrangement of surface nodes of high surface area filament construction adaptable for use as part of a tear-away fastening system. Unlike prior known practices, the composite structures of the present invention is not dependent on the formation of locking stitch segments between the outwardly projecting nodes. The quantity of yarn or other material required on a per node basis may thereby be substantially reduced relative to the yarn requirement for formation of interconnected loops in prior structures. The reduction in the length of yarn required to form a given number of hook accepting nodes across a given surface area also facilitates the use of heavier yarns which are considerably more economical on a unit weight basis.

The nodes may be formed of elongate yarn structures having a wide variety of filamentary constructions including spun yarns, multi-filament flat yarns, multi-filament textured yarns, as well as textured or flat mono-filament yarns. The nodes may be used as a female acceptance surface in a contact fastening system and/or may be subjected to further processing in the form of selective cutting and tip melting to form a male engaging surface. The resulting constructions may find uses in any number of attachment applications wherein an easily releasable fastening arrangement is desired. By way of example only, and not limitation, one such environment may be as part of a protective garment such as a diaper or the like to be worn by an infant or adult to control the discharge of bodily waste products.

BRIEF DESCRIPTION OF THE DRAWINGS

The accompanying drawings, which are incorporated in and which constitute a part of this specification illustrate exemplary constructions and procedures in accordance with the present invention and, together with the general description of the invention given above and the detailed description set forth below, serve to explain the principles of the invention wherein:

FIG. 1 illustrates a diaper incorporating a fastening arrangement utilizing cooperating hook and loop structures;

FIG. 2 illustrates schematically a procedure for forming a plurality of loops across one side of an underlying substrate with cooperating interlocking stitches across the other side of the substrate in accordance with prior art practices;

FIG. 3 is an exemplary needle point diagram illustrating a cooperating stitch forming arrangement for forming cooperating loops across a substrate according to the prior art;

FIG. 3A illustrates an arrangement of interlocking stitches across the technical face of the substrate in the stitching arrangement illustrated in FIG. 3 with the loop forming yarn segments across the technical back shown as hidden lines;

FIGS. 4A–4D illustrate steps in a practice wherein yarns are pulled through a light-weight substrate to form looped node structures across a substrate without an interlocking stitched relation between the nodes;

FIG. 5A is one exemplary needle point diagram illustrating a pattern utilized to form looped nodes across a substrate using the practice as set forth in FIGS. 4A–4D;

FIG. 5B is one exemplary needle point diagram illustrating a pattern utilized to form looped nodes across a substrate using the practice as set forth in FIGS. 4A–4D;

FIG. 6 is a scanned image of looped nodes across one side of a composite formed according to the pattern illustrated in FIG. 5A;

FIG. 7 is a schematic of a manufacturing arrangement utilizing a node formation technique as set forth in FIGS. 4A–4D and adapted to form looped nodes across a substrate using high surface area spun or filament yarns which are subjected to heat blooming;

FIG. 7A is a view similar to FIG. 7 but incorporating a tufting apparatus to effect node formation;

FIG. 7B is a view similar to FIG. 7 but incorporating a reciprocating punching apparatus to effect node formation;

FIG. 8 is a schematic illustration of a processing operation for applying a film coating across one side of a substrate layer to hold looped nodes in position across an opposing face;

FIG. 9 is a cross-sectional view of the a composite formed following the coating process illustrated in FIG. 8;

FIG. 10 is a view of a discrete looped node disposed across one side of the composite illustrated in FIG. 9 illustrating a bloomed multi-filament construction;

FIG. 11 is an alternative construction for a composite according to the present invention incorporating a substrate including a meltable film layer disposed at a position below an arrangement of looped nodes;

FIG. 11A is a view similar to FIG. 11 following activation of the meltable film layer to secure the looped nodes in position;

FIGS. 12A–12F illustrate various exemplary constructions of textured yarns adaptable for use in formation of composits according to the present invention; and FIG. 13 is a view similar to FIG. 1 in which a composite material having an arrangement of hook accepting nodes is disposed substantially across the surface of the diaper.

While the invention has been illustrated and generally described above and will hereinafter be described in connection with certain potentially preferred embodiments and practices, it is to be understood that in no event is the invention limited to such illustrated and described embodiments and practices. On the contrary, it is intended that the present invention shall extend to all alternatives and modifications as may embrace the general principles of this invention within the full and true spirit and scope thereof.

DESCRIPTION OF THE PREFERRED EMBODIMENT

Turning now to the drawings, in FIG. 1 there is illustrated a diaper 10 including a leg opening 12 and a releasable, adjustable fastening assembly. The fastening assembly incorporates a first segment of material 20 including a plurality of outwardly projecting fibrous node elements 22 and a second segment of material 24 incorporating a plurality of outwardly projecting hooking elements 26. By the term "hooking elements" is meant elements having a geometry adapted to releaseably engage the node elements 22 upon contact. By way of example only, and not limitation, such hooking elements 26 may be configured to have a hooked terminal end and/or an enlarged terminal end such as a "mushroom" shape or the like to become engaged within the node elements 22. Of course it is to be appreciated that the relative position of the first segment of material 20 incorporating the node elements 22 and the second segment of material 24 incorporating the hooking elements 26 may be reversed if desired.

It is to be appreciated that the length of one or both of the first and second segments of material 20, 24 may be adjusted so as to provide a desired arrangement for properly adjusting the diaper 10. By way of example only and not limitation, it is contemplated that in the illustrated arrangement wherein the first segment of material 20 incorporating the node elements 22 is disposed across a forward portion of the diaper 10 such first segment of material 20 may extend across an extended length thereby providing an extended surface for engagement with the second segment of material 24 during the joining process. This arrangement may facilitate adjustment of the diaper 10 to users of various size.

It is contemplated that the first segment of material 20 and/or the second segment of material 24 may be formed from a material having a plurality of loops disposed across one side. The loops across the material may be used either in loop form to define the node elements 22 in the first segment of material 20 or may be further treated to form hooks or other hooking elements 26 in the second segment of material 24 in the same manner as disclosed in U.S. Pat. No. 4,931,343.

A method as utilized to form an arrangement of loops 34 in a construction according to the prior art is illustrated in simplified form in FIGS. 2, 3 and 3A. In the prior art practice, a substrate material such as a polymeric film 30 is conveyed to a stitch-forming position. A plurality of stitching yarns 32 are stitched through the substrate 30 to form portions of the stitching yarns 32 into loops 34 projecting from the front face also known as the "technical back" of the substrate 30. As illustrated, the stitching yarns 32 are carried by yarn guides 31 such that the stitching yarns 32 are alternately engaged by reciprocating needles 36 on either side of the sinker bar fingers so as to be passed back and forth in loop-forming fashion over the associated outwardly projecting fingers of a sinker bar 38 thereby forming the loops 34 across the technical back. While for ease of reference only a single needle 36 disposed behind a sinker bar finger is illustrated, it is to be understood that in actual practice a plurality of needles 36 and corresponding stitching yarns are normally disposed across the width of the substrate 30 between spaced sinker bar fingers.

In the prior practice, the needle 36 (which is shown in greatly exaggerated dimension) pierces the substrate 30 and engages the stitching yarn 32 at a position above the sinker bar 38 such that the stitching yarn 32 is captured within a hook portion of the needle 36. As the needle 36 is reciprocated downwardly, a closing element 37 such as a closing wire which moves relative to the needle 36 closes the hook portion to hold the stitching yarn therein. With the hook portion closed, the stitching yarn 32 is pulled through an immediately preceding stitch 33 disposed around the shank of the needle 36 at a position below the substrate 30. As the stitching yarn 32 is pulled through the interior of the preceding stitch 33, the preceding stitch 33 is knocked off of the needle 36 and a new stitch is established by the portion of the stitching yarn held within the hook portion of the needle. As the needle 36 is raised back through the substrate 30 to the position illustrated in FIG. 2, the hook portion is reopened and the new stitch 33 moves out of the hook portion and is held around the shank of the needle 36 for acceptance of a subsequent stitch during the next downstroke.

A needle point diagram illustrating a typical fully threaded loop-forming stitch pattern utilized in the prior art is illustrated in FIG. 3. As will be appreciated by those of skill in the art, this construction utilizes a traditional chain stitch arrangement such that every time the yarn travels around a needle there is a yarn at the preceding needle location. That is, every time a segment of the stitching yarn 32 is pulled through the substrate, that segment engages a loop formed during the preceding stroke. This arrangement gives rise to a pattern of engaging stitches 33 (FIG. 3A) extending in substantially parallel rows in the machine direction across the surface below the substrate 30 (i.e. across the technical face) of the structure. The segments of the stitch yarns forming the loops 34 across the technical back are shown as hidden lines.

As shown, in the prior art practice, the engaging stitches 33 cooperate with one another in the machine direction of the fabric in a substantially stable interlocking relation thereby anchoring the yarns in place. A break in this sequence results in the loss of this anchoring relation thereby permitting the yarn 32 to be pulled easily out of the substrate 30. As will be appreciated, the use of the illustrated prior art stitch forming practice produces stable loops 34 across one side of the substrate 30 held in place by the underlying stitches 33 across the opposing side of the substrate 30. However, such a construction may require a relatively high quantity of stitching yarn 32 to form the stitches 33 across the side of the substrate facing away from the loops 34. This relatively high yarn consumption arises from the fact that a stable anchoring relation between the loops 34 and the stitches 33 is dependent upon a stitch and associated loop being formed at every needle in every cycle in order to avoid a break in the sequence.

The various practices according to the present invention do not rely upon the formation of interlocking stitches to anchor loop forming yarns in place. Rather, the practices of the present invention utilize various yarn insertion techniques to form an arrangement of node elements across one side of a substrate.

The yarn forming the node elements is preferably of a fibrous textured yarn construction such as a spun yarn, multi-filament textured yarn having an arrangement of entangled filaments, mono-filament textured yarn incorporating an arrangement of raised surface fibrils or the like affording a high surface area for engagement with cooperating hooking elements. In this regard, it is contemplated that particularly useful textured filament yarn constructions may include multi-filament or mono-filament yarns which have undergone various treatments to impart texture including, by way of example only and not limitation, entanglement, abrasion, crimping, twisting, chemical degradation, irradiation and the like including combinations of such treatments so as to impart an enhanced surface area to the yarns. Spun yarn constructions may be used in the as-spun state or may be subjected to any suitable additional texturizing process as may be desired. As will be discussed further hereinafter, it is also contemplated that the effective surface area of textured yarn constructions forming the node elements may be further enhanced by subjecting such yarns to so called "blooming treatments" before and/or after insertion through the substrate. Of course, flat yarns of multi-filament or mono-filament construction may also be utilized if desired.

After yarn insertion has taken place, a bonding layer of polymeric tie coat material is preferably disposed across the side of the substrate facing away from the node elements thereby locking the node elements in place. Thus, the prior constraint of forming interlocking stitches and associated loops in a substantially one to one relationship at every needle location is avoided. This, in turn, permits nodes to be formed at virtually any desired concentration per unit area across the substrate. Since stitches are not required to lock loops in place, it may be possible to utilize less yarn. Moreover, since the overall length of yarn required is substantially reduced, heavier (i.e. higher denier) yarns may be used without introducing excessive weight. As will be appreciated, such higher denier yarns are typically more economical on a per weight basis and may be easier to process during actual construction. In addition, the elimination of the need to form interlocking stitches across the side of the substrate facing away from the loops provides the ability to utilize a wide array of insertion techniques.

One exemplary practice for forming a composite material which may thereafter be used as a segment of a tear away fastening system is illustrated in FIGS. 4A–4D wherein elements corresponding to those previously illustrated and described in relation to FIG. 2 are designated by like reference numerals increased by 100. As illustrated, in this process node-forming yarn 132 does not engage the fingers of the sinker bar 138. Rather the sinker bar 138 is used primarily to hold the substrate 130 in place as the node-forming yarn is periodically pulled through the substrate 130 so as to form a plurality of looped node elements 134 across the back side or so-called "technical face" of the substrate 130.

In the practice illustrated in FIGS. 4A–D, a substrate 130 is conveyed under tension to a needle engagement position at which a reciprocating needle 136 moves through the substrate. During formation, a plurality of node-forming yarns carried by dynamic yarn guides 131 are engaged by reciprocating needles at a position above the substrate 130 in the manner as previously described. While for ease of reference only a single needle 136 disposed behind a sinker bar finger is illustrated, it is to be understood that in actual practice a plurality of needles 136 and corresponding node-forming yarns 132 are normally disposed across the width of the substrate 130 (i.e. in the cross machine direction) between spaced sinker bar fingers.

In the illustrated practice the needle 136 (which is shown in greatly exaggerated dimension) pierces the substrate 130 and engages the node-forming yarn 132 supported by a moveable yarn guide 131 at a position above the substrate 130 such that the node-forming yarn 132 is captured within a hook portion of the needle 136 (FIG. 4A). As the needle 136 is reciprocated downwardly, a closing element 137 such as a closing wire which moves relative to the needle 136 closes the hook portion to hold the stitching yarn therein as it is pulled through the substrate 130. Contrary to the prior art practice, no immediately preceding stitch is disposed around the shank of the needle 136 below the substrate 130. Thus, as the stitching yarn 132 is pulled through the substrate 130 and away from the underside of the substrate 130, a looped node 134 is thereby formed across the technical face (FIG. 4B).

After formation of the looped node 134, the needle 136 is raised and the hook portion is reopened thereby permitting the looped node 134 formed on the downstroke to slide out of the hook portion and around the shank of the needle 136 (FIG. 4C). On the next downstroke, the yarn guide 134 is shifted away from the needle path such that the node forming yarn 132 does not engage the needle 136. As the needle 136 travels downwardly, the previously formed looped node 134 is knocked off of the needle 136 (FIG. 4D). A series of discrete looped nodes 134 is thus formed across the technical face with intermediate yarn segments 145 extending between the looped nodes 134 across the technical back.

As will be appreciated, during the downstroke of the needle 136 when the node-forming yarn is not engaged, it is contemplated that the node-forming yarn 132 may either remain disengaged from any needle or may engage an adjacent needle (not shown). In the event that an adjacent needle is engaged, the node-forming yarn 132 is pulled through the substrate 130 and forms a looped node in adjacent diagonal relation to the first formed looped node. Of course it is to be understood that any number of arrangements for the engagement and disengagement of the node forming yarn 132 by needles 136 may be used to form a desired concentration and pattern of looped nodes 134 across one side of the substrate 130 with intermediate yarn segments 145 disposed across an opposing side of the substrate 130.

By way of example only, in FIG. 5A a needle point diagram is provided illustrating a half threaded tricot stitch arrangement as may be used in practice of the present invention. As will be appreciated by those of skill in the art, in this arrangement loops defining nodes are formed at every other needle point along needle lines with the node-forming yarn 132 shifting back and forth between adjacent needle lines. Another contemplated arrangement is illustrated in FIG. 5B. In this arrangement the node-forming yarns 132' form loops so as to define an arrangement of nodes at needle points disposed along multiple lines before shifting back to the starting needle line. It is also contemplated that the node-forming yarns need not shift between needle lines in which case the yarns will be arranged in a straight line along the machine direction with a profile geometry corresponding generally to a sine wave.

By using any of these insertion arrangements, a construction may be formed in which the yarn intentionally skips engagement with the needle in a needle line according to a predefined sequence thereby avoiding the formation of a substantially continuous stitch pattern along the needle line. Of course, loop forming arrangements other than those illustrated may likewise be utilized if desired. Generally, it is contemplated that any number of partially threaded yarn insertion patterns may be utilized where engagement between the yarn 132 and the needle 136 is skipped at one or more needle points between loops along each needle line.

As will be appreciated by those of skill in the art, the failure of the node-forming yarn 132 to engage the needle 136 at each needle point along the needle line gives rise to a so-called "drop stitch" phenomenon. Such a drop stitch would normally be considered to be a defect in a traditional product due to the fact that the loop formed lacks an anchoring relation across the side of the substrate facing away from the loop. That is, the intermediate yarn segments 145 extending across the technical back are not stitched into a cooperating structure across the technical back. The intermediate yarn segments 145 can thus be pulled freely away from the technical back which in turn permits the associated opposing looped nodes 134 to be pulled out of the technical face. However, in the present invention the absence of a traditional stitched relation is utilized intentionally to substantially reduce the overall quantity of yarn disposed across the side of the substrate facing away from the looped nodes 134 and thereby reducing the overall quantity of node forming yarn 132 required.

Due to the fact that the node-forming yarn 132 is not anchored in place within the substrate 130, it is contemplated that a backing layer 140 such as a preformed polymeric adhesive film, thermoplastic coating, heat cureable dispersion or the like may be applied across the technical back of the material as it is formed. Of course, it is contemplated that other stabilizing materials may be utilized if desired. By way of example only, according to one contemplated practice, the backing layer 140 may be a thermoplastic coating applied by a continuous slot die or extrusion coater as will be well known to those of skill in the art. One such thermoplastic coating may be made up of a low density polyethylene (LDPE) polymer although other materials may likewise be utilized. As will be appreciated, in such a construction the backing layer 140 is melt bonded in affixed relation to the side of the substrate 130 facing away from the looped nodes 134. According to another contemplated practice, the backing layer 140 may be an aqueous dispersion such as SBR latex applied by a spraying or roll coating process.

In the exemplary arrangement illustrated in FIGS. 4A–4D, the introduction of the backing layer is illustrated as taking place substantially in line with the formation of the looped nodes 134. It is contemplated that such an arrangement may be particularly useful if the backing layer 140 is in the form of a preformed adhesive sheet or the like. If the backing layer is to be introduced in the form of a dispersed coating such as by use of a slot die extruder or the like, it is contemplated that such application may be carried out more efficiently on a separate coating line such as is illustrated schematically at FIG. 8, although direct in-line processing may likewise be utilized if desired.

As previously indicated, the substrate 130 may be of a generally low strength material. By way of example only and not limitation, contemplated substrate materials may include light weight fibrous webs of needle punched, hydroentangled, or spun bonded fibers with relatively low levels of coherency between the fibers. Light weight polymer or metalic films may also be utilized. Very light weight gossamer-like spun bonded polyester or polypropylene having a mass per unit area of about 15 grams per square meter may be particularly preferred. As will be appreciated, such materials provide little structural integrity. Accordingly, in such constructions the backing layer 140 may serve the dual roles of providing strength to the overall composite as well as anchoring the yarn in place. If desired, it is also contemplated that the node-forming yarn and/or the substrate 130 may include a thermoplastic constituent to facilitate heat activated bonding of the yarns within the substrate so as to improve positional stability.

In FIG. 6, a scanned image is provided illustrating an exemplary stitch bonded structure formed according to the needle point diagram illustrated in FIG. 5A with looped nodes 134 formed across one side of an underlying nonwoven substrate 130. As will be appreciated, the looped nodes 134 are formed at alternating needle points where the needle 136 has engaged the node-forming yarn 132 and pulled it through the substrate 130. Thus, the looped nodes 134 are arranged in substantially parallel rows extending in the machine direction of the formed composite. Intermediate yarn segments 145 extend between the looped nodes 134 across the underside of the nonwoven substrate. As can be seen, the intermediate yarn segments 145 are visible through the substrate 130 due to the light construction of the substrate 130.

As previously indicated, the node-forming yarns may be of a wide variety of yarn constructions including untextured mono-filaments, texturized mono-filaments, spun yarns, flat (i.e. untextured) multi-filament yarns, and textured multi-filament yarns including entangled constructions, false twist constructions, topically abraded constructions, chemically degraded constructions, irradiated constructions, physically deformed constructions and the like as will be well known to those of skill in the art. It is contemplated that the use of multi-filament textured yarn constructions may be particularly beneficial in some applications so as to enhance the effective surface area of the nodes projecting away from the substrate. In turn, the enhancement of this effective surface area is believed to enhance the locking character of the nodes when used in a contact fastening system. The use of such textured yarn to form nodes according to the present invention may be particularly beneficial in constructions for use as female acceptance portions of a contact fastening system.

Turning to FIG. 7, a schematic illustration of a process for forming an arrangement of node elements 234 across one side of a substrate 230 using a node forming yarn 232 of textured construction is provided. As illustrated, in this process the node forming yarn 232 is delivered from a beam 250 over a roller 251 to a tensioning roll 254 of rubber or the like. As will be appreciated, the presence of the tensioning roll 254 upstream of the yarn guide 231 facilitates the withdrawal of the yarn from the beam 250 while nonetheless permitting the node-forming yarn 232 to be transferred to the needle 236 at very low tension.

In the illustrated practice, following withdrawal from the beam 250, the node-forming yarn 232 is preferably subjected to a blooming treatment in the form of contacting or non-contacting heat application by a heater 256 such as a heated platen, hot air blower or the like. As will be appreciated, the application of heat following withdrawal of the node-forming yarn from the beam 250 causes a blooming or spreading of the individual filaments making up the node-forming yarn thereby giving rise to a slight degree of separation between the individual filaments.

Following the initial blooming treatment of the node-forming yarn 232, the node-forming yarn is transferred to the needle engagement zone for insertion by the needle 236 through a substrate 230 delivered from a roll 235. The substrate 230 is preferably of a light weight construction as previously described and insertion of the node-forming yarn is preferably carried out in the manner as previously described so as to form an arrangement of looped nodes 234 without interlocking stitching between intermediate yarn segments 245. Following insertion of the node-forming yarn, the formed composite is thereafter preferably delivered to a second heater 258 such as a heated platen, hot air blower or the like to effect final blooming of the node-forming yarn 232 and to relieve any compaction of the yarn fibers which may result from the insertion process. Of course, it is contemplated that one or the other of the heaters 256, 258 may be eliminated if desired. The composite material is thereafter delivered to a take-up roll 259 to await subsequent application of a backing layer as will be described further hereinafter.

While it is contemplated that reciprocating needles may be used to efficiently carry out yarn insertion so as to form looped nodes across one side of a substrate, it is likewise contemplated that any number of other manual or automated formation techniques may also be utilized. By way of example only, in FIG. 7A an alternative formation process is illustrated wherein elements corresponding to those previously described are designated by like reference numbers within a 300 series. As shown, this process corresponds substantially to that illustrated and described in relation to FIG. 7 with the exception that the reciprocating needles are replaced by a pair of tufting needles 360 which cooperatively insert and withdraw a node-forming yarn 332 as previously described through a substrate 330 as previously described so as to form an arrangement of looped nodes 334 across one face of the substrate. Of course, such a process may be used with any of the yarns previously described, but may be most suitable for yarns of relatively high denier.

By way of further example, in FIG. 7B an alternative formation process is illustrated wherein elements corresponding to those previously described are designated by like reference numbers within a 400 series. As shown, this process corresponds substantially to that illustrated and described in relation to FIG. 7 with the exception that the reciprocating needles are replaced by reciprocating needles 462 of open forked construction. As will be appreciated, the needles 462 are adapted to periodically engage the node-forming yarn 432 as previously described at a position above a substrate 430 as previously described and thereafter push that yarn 432 through the substrate 430 to form an arrangement of looped nodes across the underside of the substrate 430.

As previously indicated, it is contemplated that a backing layer in the form of an extruded polymer film may be applied at a position below the substrate 230 thereby acting as a tie coat layer to anchor the looped nodes in place across an opposing side of the substrate. In FIG. 8 a schematic is provided of an exemplary processing line as may be used in the application of such an extruded polymer film. As will be appreciated, while the reference numerals utilized in FIG. 8 correspond to those utilized to designate like elements in FIG. 7, it is contemplated that such a processing line may be used to coat composite yarn and substrate structures formed by any of the processes and materials previously described. According to the illustrated process, a previously formed composite structure of yarn inserted through a substrate as described is delivered from a roll 259 to a slot die extruder 270 such that a polymeric coating composition 272 such as low density polyethylene (LDPE) is deposited in a relatively thin film-forming layer across the side of the composite facing away from the looped nodes 234. A back coated composite structure 280 is thereby formed in which the polymeric coating composition defines a backing layer 240 (FIG. 9) having an effective thickness to hold the intermediate yarn segments 245 in place. Preferably, the thickness of the backing layer is sufficient to cover the intermediate yarn segments 245 although it is also contemplated that portions of the intermediate yarn segments 245 may remain exposed if desired.

Of course, polymeric coating compositions other than LDPE may likewise be utilized if desired. By way of example only, other thermoplastic coating compositions as may be used include so called hot melt adhesives such as those based on bitumen or polyurethane. It is also contemplated that thermosetting compositions such as SBR latex and the like may be utilized if desired. In such a construction, the extruder 270 may be replaced by a spray coater, roll coater or the like followed by a heater at which the applied thermosetting composition is cured.

FIG. 9 illustrates an exemplary back coated composite structure 280 formed in accordance with the present invention using a textured yarn inserted though a nonwoven substrate and FIG. 10 illustrates the detail of a representative looped node formed from a bloomed textured yarn. As previously indicated, it is contemplated that a textured multi-filament yarn construction may be beneficial in enhancing the attachment character of the nodes by providing a substantially enhanced effective surface area for use in contacting cooperating hook structures in a contact attachment structure. In particular, in each looped node 234 a number of filament loops 282 are available on both an individual and collective basis for latching attachment to cooperating hook structures. Accordingly, if blooming is carried out effectively, the filament loop density, and thus the number of attachment zones per unit area may be dramatically increased over traditional mono-filament yarns which provide a single filament per loop. A bloomed textured multi-filament yarn may also provide enhanced hook retention strength over structures incorporating flat yarns wherein a smaller percentage of filaments are available for hook attachment due to the tight bundled nature of the filament arrangement.

Aside from the substrate and separately applied backing layer previously described, it is also contemplated that the looped nodes may be held in place by a wide variety of other anchoring systems. By way of example only, and not limitation, according to one system it is contemplated that a node-forming yarn may be inserted through a multi-layer backing 586 (FIG. 11) so as to form an arrangement of looped nodes 534 above the multi-layer backing 586 with intermediate yarn segments 545 disposed across the underside of the multi-layer backing 586. In such a system, a lower layer 588 may be in the form of a polymeric film or the like having a relatively lower melting point than a polymeric film or other material forming an upper layer 587. Thus, as illustrated in FIG. 11A, upon the application of heat the lower layer 588 may undergo selective softening or melting so as to coalesce around the intermediate yarn segments 545 thereby anchoring the intermediate yarn segments 545 in place.

Due to the fact that the inserted yarns are not required to provide substantial structural integrity to the system of the present invention, it is contemplated that the present invention may afford additional flexibility in the selection of yarn types for use in the formation of the nodes. In this regard it is contemplated that virtually any yarn type as may be desired may be utilized. By way of example only, contemplated yarn materials include polyester, polypropylene and nylon. Moreover, a wide range of linear densities may be utilized in the yarns. By way of example only, and not limitation it is contemplated that the yarns used to form the looped nodes may be characterized by a linear density in the range of about 40 denier to about up to about 1000 denier or more.

As previously indicated, although flat and spun yarn constructions are contemplated and may be desirable in some applications, textured yarn constructions may offer some performance advantages in other applications. Moreover, it is contemplated that textured yarns of various constructions may provide a potentially desirable enhanced frictional character to the yarn which may aid in yarn insertion and anchoring within an underlying substrate. By way of example only, and not limitation, various textured yarn constructions which may be used for insertion may include entangled yarn (FIG. 12A); knit-de-knit crinkle yarn (FIG. 12B); multi-filament coil yarn (FIG. 12C); mono-filament coil yarn (FIG. 12D); stuffer box crinkle yarn (FIG. 12E); and bulked core and effect yarn (FIG. 12F). Of course, this listing is exemplary only and virtually any other textured yarn construction as may be known to those of skill in the art may likewise be utilized.

Aside from possible processing and performance characteristics, it is also contemplated that a fabric structure formed according to the present invention utilizing a textured yarn will have desirable aesthetic and tactile characteristics making it potentially desirable as a partial or complete outer surface covering for a diaper. That is, due to the textured surface of the looped nodes, such nodes will tend to define an outer surface of substantially soft character emulating a natural fiber fleece or the like. At the same time, the looped nodes are suitable for engagement by cooperating hooking structures to fasten segments together. By way of example only, and not limitation, in FIG. 13 there is illustrated a diaper 210 including a leg opening 212 and an outer surface covering of composite material 280 including a covering of looped nodes such as that illustrated in FIG. 9. The diaper 210 further includes a hooking tab 224 including an arrangement of hooks 226 for cooperative engagement with any portion of the outer surface covering so as to effect closure of the diaper 210.

It is to be understood that while the present invention has been illustrated and described in relation to certain potentially preferred embodiments, constructions and procedures, that such embodiments, constructions and procedures are illustrative only and that the present invention is in no event to be limited thereto. Rather, it is contemplated that modifications and variations embodying the principles of this invention will no doubt occur to those of to those of skill in the art in the art. It is therefore contemplated and intended that the present invention shall extend to all such modifications and variations as may incorporate the broad aspects of the invention within the full spirit and scope thereof.

What is claimed is:

1. A method for forming a composite sheet material adapted to be cut into smaller pieces to form a female portion of a tear away fastener system for a diaper, said method comprising the steps of:

providing a substrate layer having a first face and a second face projecting away from said second face;

providing a plurality of yarns of textured multi-filament construction to positions in spaced opposing relation to said second face, wherein said yarns includes plurality of discrete filaments;

blooming said plurality of yarns by application of heat so as to at least partially spread said filaments apart;

pulling segments of said plurality of yarns through said substrate layer from the positions in spaced opposing relation to said second face using reciprocating needles that hookingly engage said plurality of yarns such that the segments pulled through the substrate layer form a plurality of looped elements projecting away from said first face and such that segments of said plurality of yarns between said looped elements project away from said second face of said substrate layer, wherein upon hooking engagement between said reciprocating needles and said plurality of yarns said reciprocating needles project across said substrate layer from positions opposing said first face and wherein said plurality of yarns are manipulated in a predefined manner by moveable yarn guide elements such that during a given cycle of penetration and withdrawal of said reciprocating needles across the substrate layer, at least a portion of said plurality of yarns are shifted away from hooking engagement with the reciprocating needles that engaged said at least a portion of said plurality of yarns during an immediately preceding cycle of penetration and withdrawal and such that during said given cycle of penetration and withdrawal at least a portion of the reciprocating needles that engaged said at least a portion of said plurality of yarns during said immediately preceding cycle do not do not pull any segment of yarn through the substrate layer upon withdrawal from the substrate layer, such that a predefined pattern of needle punctures containing yarn segments defining base segments of looped elements is formed across the substrate layer in combination with empty needle punctures disposed in a predefined pattern between at least a portion of the looped elements, whereby the number of looped elements is less than the total number of needle punctures; and anchoring said yarns in position within said substrate layer by means of a substantially resilient polymeric material defining a backing layer disposed at least partially around segments of said plurality of yarns projecting away from said second face of said substrate layer.

2. The invention as recited in claim 1, wherein said yarns are characterized by a linear density in the range of about 40 denier to about 1000 denier.

3. The invention as recited in claim 2, wherein said multi-filament yarns comprise synthetic materials selected from the group consisting of polyester, polypropylene, and nylon.

4. The invention as recited in claim 2, wherein said substrate layer comprises a web of entangled synthetic fiber elements.

5. The invention as recited in claim 4, wherein said web of entangled synthetic fiber elements is of a spun bonded construction.

6. The invention as recited in claim 5, wherein said web of entangled synthetic fiber elements is characterized by a mass per unit area of about 15 grams per square meter.

7. The invention as recited in claim 1 wherein said substrate layer consists essentially of at least one layer of polymeric film.

8. The invention as recited in claim 1, wherein said backing layer comprises a thermoplastic coating extrusion coated across said second face of said substrate layer.

9. The invention as recited in claim 1, wherein said blooming step is carried out before and after the inserting step.

10. The invention as recited in claim 9, wherein the anchoring step comprises extrusion coating a layer of thermoplastic polymeric material across said second face of said substrate layer.

11. The invention as recited in claim 10, wherein the thermoplastic polymeric material is low density polyethylene.

12. A method for forming a composite sheet material adapted to be cut into smaller pieces to form a female portion of a tear away fastener system for a diaper, said method comprising the steps of:

providing a substrate layer having a first face and a second face projecting away from said second face;

providing a plurality of yarns of textured multi-filament construction to positions in spaced opposing relation to said second face, wherein said yarns include a plurality of discrete filaments;

inserting segments of said plurality of yarns through said substrate layer from the positions in spaced opposing relation to said second face using reciprocating needles that engage said plurality of yarns such that the segments inserted through the substrate layer form a plurality of looped elements projecting away from said first face and such that segments of said plurality of yarns between said looped elements project away from said second face of said substrate layer, wherein said plurality of yarns are manipulated in a predefined manner by moveable yarn guide elements such that during a given cycle of penetration and withdrawal of said reciprocating needles across the substrate layer, at least a portion of said plurality of yarns are shifted away from engagement with the reciprocating needles that engaged said at least a portion of said plurality of yarns during an immediately preceding cycle of penetration and withdrawal and such that during said given cycle of penetration and withdrawal at least a portion of the reciprocating needles that engaged said at least a portion of said plurality of yarns during said immediately preceding cycle do not do not insert any segment of yarn through the substrate layer, such that a predefined pattern of needle punctures containing yarn segments defining base segments of looped elements is formed across the substrate layer in combination with empty needle punctures disposed in a predefined pattern between at least a portion of the looped elements, whereby the number of looped elements is less than the total number of needle punctures;

anchoring said yarns in position within said substrate layer by extrusion coating a substantially resilient polymeric material across said second face of said substrate layer such that said substantially resilient polymeric material is disposed at least partially around segments of said plurality of yarns projecting away from said second face of said substrate layer; and blooming said plurality of yarns by application of heat so as to at least partially spread said filaments apart.

13. The invention as recited in claim 12, wherein said substrate layer comprises a web of entangled synthetic fiber elements of spun bonded construction.

14. The invention as recited in claim 13, wherein said web of entangled synthetic fiber elements is characterized by a mass per unit area of about 15 grams per square meter.

15. The invention as recited in claim 12 wherein said substrate layer consists essentially of at least one layer of polymeric film.

* * * * *